US00PP30303P3

(12) United States Plant Patent
Hansen

(10) Patent No.: US PP30,303 P3
(45) Date of Patent: Mar. 19, 2019

(54) ***HOSTA* PLANT NAMED 'WATERSLIDE'**

(50) Latin Name: ***Hosta* hybrid (Tratt.)**
Varietal Denomination: Waterslide

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 77 days.

(21) Appl. No.: 15/731,018

(22) Filed: Apr. 7, 2017

(65) Prior Publication Data

US 2018/0295763 P1 Oct. 11, 2018

(51) Int. Cl.
*A01H 5/12* (2018.01)
*A01H 6/12* (2018.01)

(52) U.S. Cl.
USPC ..... Plt./353
CPC ..... *A01H 6/12* (2018.05)

(58) Field of Classification Search
USPC ..... Plt./353
CPC ..... A01H 5/02; A01H 5/0272; A01H 5/12; A01H 5/00; A01H 6/12; A01H 6/56
See application file for complete search history.

(56) References Cited

PUBLICATIONS

Botanophilia LLC, New Plants for 2017 dated Dec. 14, 2016, retrieved on Apr. 3, 2018, retrieved from the Internet at http://www.iloveshadeplants.com/2016/12/new-plants-for-2017.html, 2 pages. (Year: 2016).*

* cited by examiner

*Primary Examiner* — June Hwu

(57) ABSTRACT

A new and distinct *Hosta* plant named 'Waterslide' with compact rounded-mound habit of dense bluish-colored, lanceolate foliage having wavy margins, narrowly acute apex and cordate base and are longitudinally folded upward at the midrib. The bluish coloring, coming from thick glaucous covering remains through the flowering season until the end of summer. The plant has lavender flowers densely arranged on bluish-colored stapes just above the foliage.

2 Drawing Sheets

Latin name and variety denomination of the plant:
Botanical classification: *Hosta* hybrid (Tratt.).
Variety denomination: 'Waterslide'.

FEDERALLY SPONSORED RESEARCH

This invention was developed without any federally sponsored research or development funding.

BACKGROUND AND ORIGIN OF THE PLANT

The present invention relates to a new and distinct *hosta* plant, *Hosta* 'Waterslide' hereinafter also referred to as the new plant or just the cultivar name, 'Waterslide'. *Hosta* 'Waterslide' was hybridized at a wholesale nursery in Zeeland, Mich., USA in the summer of 2010 as a cross between the unreleased proprietary hybrid known as "WGI 16" (not patented) and the male parent 'Neptune' U.S. Plant Pat. No. 19,674. WGI 16 is a complex hybrid involving 'Medusa' (not patented), a selection of *Hosta venusta* (not patented), 'Blue Moon' (not patented) and a selection of *Hosta pychnophylla* (not patented). The new plant is the selection of as a single seedling among several in that cross identified as H10-177-1 through the trial process. The new plant has been asexually propagated by division at the same nursery in Zeeland, Mich., USA since 2014 and also by careful plant shoot-tip tissue culture with the resultant asexually propagated plants having retained all the same traits as the original plant.

No plants of *Hosta* 'Waterslide' have been sold, under this or any other name, in this country or anywhere in the world, prior to the filing of this application, nor has any disclosure of the new plant been made prior to the filing of this application with the exception of that which may have been sold or disclosed within one year of the filing date of this application and was either derived directly or indirectly from the inventor.

BRIEF SUMMARY OF THE PLANT

There are over 5,600 registered *hosta* cultivars with The American *Hosta* Society, which is the International Cultivar Registration Authority for the genus *Hosta* along with a similar number of unregistered cultivars. The nearest known comparison cultivars are is *Hosta* 'Joy Ride' (not patented), 'Neptune' U.S. Plant Pat. No. 19,674, 'Salute' (not patented), 'Cutting Edge' (not patented), 'Venetian Blue' (not patented) and 'Yankee Blue'.

'Joy Ride' has leaves that are less sinuate and loses their bluish coloring earlier and slightly lustrous foliage above and below but does not have the longitudinal folding. 'Neptune' has bluish glaucous coating on the foliage and lacks the folding. 'Salute' has a more upright habit and the foliage has a slight wave but not the intense sinuate margin, folding or bluish glaucous coloring. 'Cutting Edge' has a similar habit, but the foliage is larger, less sinuate and less bluish coloring. 'Venetian Blue' is larger in habit with smaller leaves that do not have the sinuate margin, the folding or intense glaucous blue of the new plant 'Yankee Blue' has a larger habit and the foliage lacks the bluish coloration, the sinuate margin and the folding. None of the above plants retain the glaucous bluish coloring of the foliage as late in the season as 'Waterslide', and the new plant is smaller and more compact than all of the above cultivars.

The female parent, WGI 16 is smaller in habit with more rounded foliage.

Other *Hosta* cultivars have glaucous foliage, but 'Waterslide' is distinct from the above listed *hostas* and all other cultivars known to the discoverer by the following combined traits:

1. Compact rounded-mound plant habit with dense bluish-colored foliage;
2. Lanceolate foliage with sinuate margins, narrowly acute apex and cordate base;
3. Leaves with bluish coloring above, also easily visible below due to longitudinal folding along the midrib;
4. Leaves retain their glaucous bluish coloring until the end of the summer; and
5. Tightly-compact lavender flowers on bluish-colored scapes just above foliage.

BRIEF DESCRIPTION OF THE DRAWINGS

The photographs of the new plant demonstrate the overall appearance of the new plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
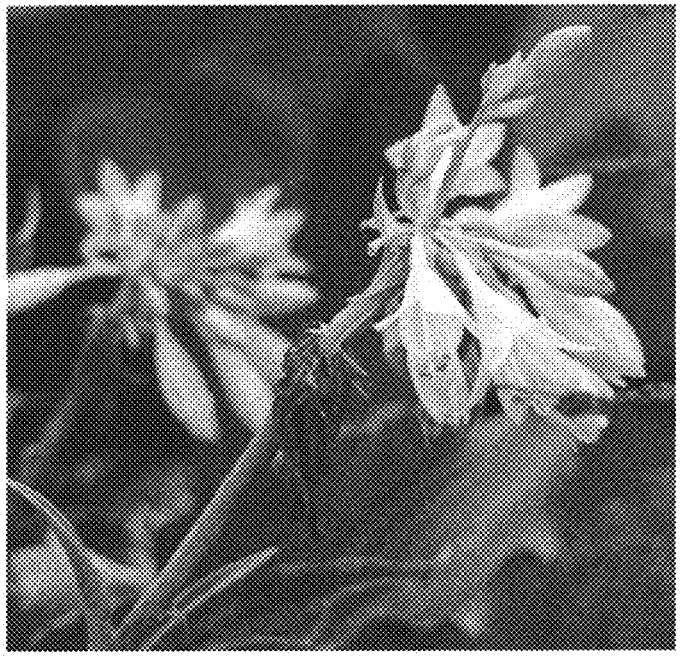
FIG. 1 shows a close-up of the flowering scape.
Figure 2:
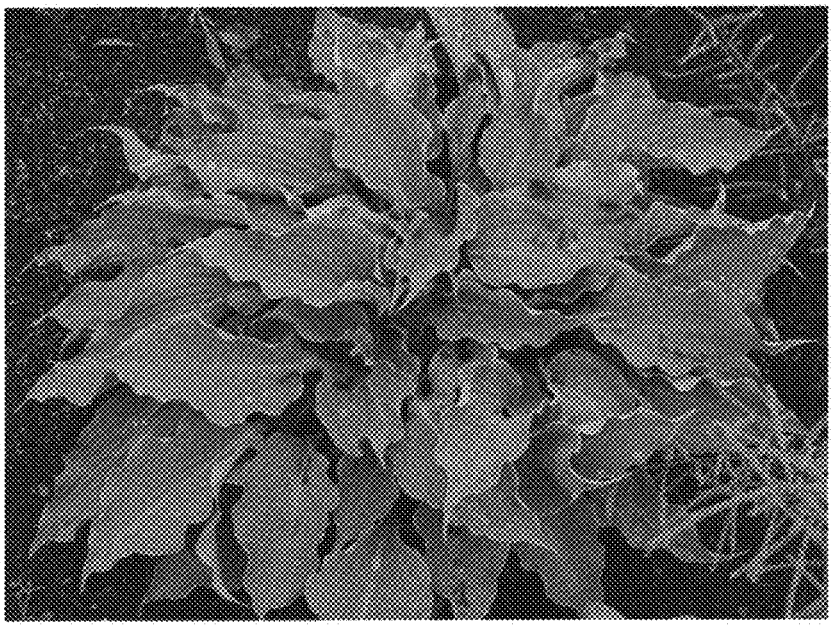
FIG. 2 shows a six-year-old plant in the landscape with bluish, folded, sinuate foliage.
Figure 3:
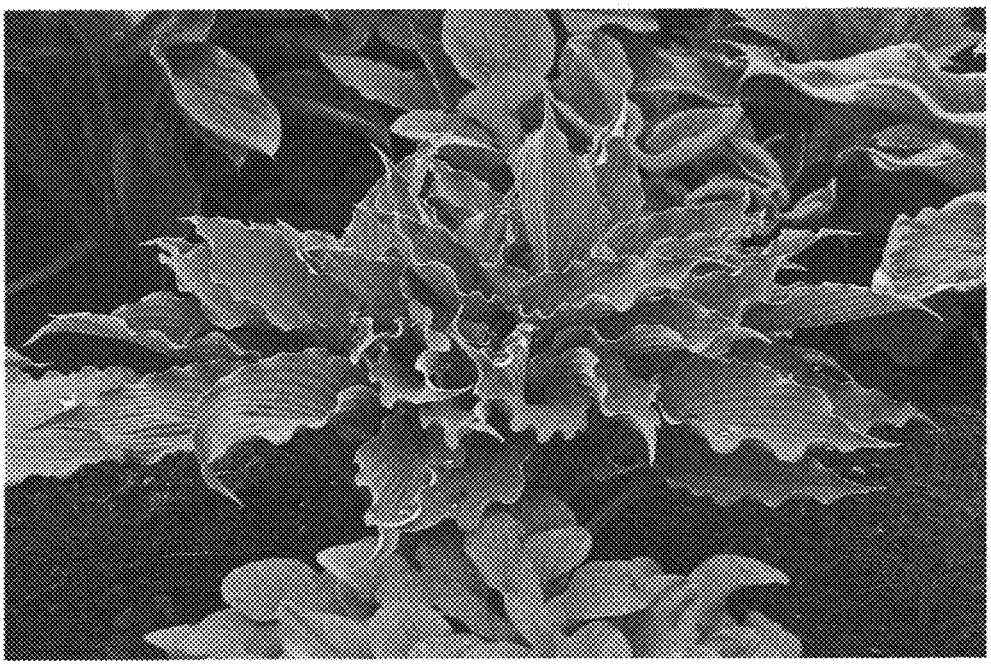
FIG. 3 shows a side view of a five-year-old plant showing the upright, mounded plant habit.

The following descriptions and color references are based on the 2001 edition of The Royal Horticultural Society Colour Chart except where common dictionary terms are used. The new plant, *Hosta* 'Waterslide', has not been observed under all possible environments. The phenotype may vary slightly with different environmental conditions, such as temperature, light, fertility, moisture and maturity levels, but without any change in the genotype. The following observations and size descriptions are of a six-year old plant in a partially shaded trial garden in Zeeland, Mich. with supplemental water and fertilizer.

Botanical classification: *Hosta* x hybrid;

Parentage: Hybrid of WGI 16 as the female parent, and 'Neptune' as the male parent;

Propagation: Garden division and sterile shoot-tip tissue culture;

Time to initiate roots from tissue culture: About two to three weeks;

Growth rate: Rapid;

Crop time: About 10 to 12 weeks to finish during the summer in a one-liter container from rooted tissue culture plantlet;

Rooting habit: Normal, fleshy, lightly branching;

Plant shape and habit: Hardy herbaceous perennial with basal rosette of leaves emerging from rhizomes producing a short symmetrical upright, rounded-mound of leaves;

Plant size: Foliage height about 32.0 cm above soil line to the top of the leaves and about 80.0 cm wide at the widest point slightly above the soil line;

Foliage description: Glabrous, heavily glaucous abaxial and adaxial; lanceolate, with narrowly acute apex and cordate base; entire coarsely-sinuate margin; without blistering or dimples between the veins; blades flat, without twisting;

Leaf blade size: To about 21.0 cm long, 11.2 cm wide at base and folded to 4.2 cm deep at midrib; average about 17.5 cm long, 9.5 cm wide and 3.5 cm deep;

Leaf blade color: Early season and shortly after emerging adaxial and abaxial color blend between RHS 122A and RHS 188A; mid-season and later summer adaxial blend between RHS 122A and RHS 188A; mid-season and later abaxial blend between RHS 122A and RHS 188C;

Petiole: Entire, glabrous, glabrous, concavo-convex; mostly straight from base of plant to leaf base with little bending or curving, strong but flexible; to about 22.0 cm long and 1.5 cm wide at base, average 20.0 cm long and 1.3 cm wide at base;

Petiole color: Adaxial center between RHS N144A and RHS 145A and margin nearest RHS 137C; abaxial center nearest RHS 145C and margin nearest RHS 137C;

Veins: Parallel, impressed adaxial or moderately bulging and costate on abaxial side; average about ten pairs and one main center vein;

Veins color: Adaxial midrib between RHS N144A and RHS 145A with secondary veins the same color as the surrounding tissue; abaxial midrib nearest RHS 137C and secondary veins nearest RHS 146B;

Flower description:

Buds one day prior to opening: Clavate with acute apex and narrow tubular base; entire bud about 3.0 cm long, with swollen distal portion about 8.0 mm diameter and about 12.0 mm long, base tube about 8.0 mm long and about 3.0 mm diameter, flowers slightly smaller distally;

Bud color: Base nearest RHS 76C; apical swollen portion between RHS N81B and RHS N81C;

Flowers: Perfect; actinomorphic; funnelform; held slightly drooping to outwardly; about 3.2 cm wide and 4.5 cm long, fused tube portion about 1.0 cm long and 3.5 mm diameter (distal flowers smaller); persists for a normal period, usually one day on plant or as cut flower; scapes remain effective with flowers beginning late July through late August for about four weeks in Michigan; about 40 flowers per scape; held in four or five whorls of about eight to ten flowers;

Floral bracts: Subtending flowers; lanceolate, acute apex, truncate partially clasping base; to about 2.5 cm long and 1.0 cm wide; concavo-convex;

Floral bract color: Abaxial nearest RHS N81D both abaxial and adaxial;

Flower fragrance: None detected;

Tepal: Six; two sets of three, glabrous, entire; oblong to lanceolate with acute apex and fused base; both sets medium length, approximately 4.3 cm long and about 1.3 cm wide;

Tepal color: Abaxial inner set with 2.0 mm white margin lighter than RHS 155D, becoming transparent in outer 0.5 mm, longitudinal center portion nearest RHS 76C with darker midrib between RHS 76A and RHS 76B; abaxial outer set between RHS 76A and RHS 76B with lighter near white margin about 0.5 mm wide lighter than RHS 76D; adaxial inner set 4.5 mm wide white margin lighter than RHS 155D, longitudinal center 2.5 mm wide portion lighter than RHS N81D with three darker veins nearest RHS N80C; adaxial outer set with 2.5 mm white margin lighter than RHS 155D, longitudinal center 2.5 mm wide lighter than RHS 81D with three darker veins nearest RHS N80C;

Gynoecium: Single; tri-carpelled;

*Style*.—Single, approximately 4.3 cm long, 1.0 mm diameter, arcuate upward about 70° in distal 5.0 mm; color nearest RHS 11D.

*Stigma*.—Globose, about 1.0 mm in diameter; color nearest RHS 11D.

*Ovary*.—Oblong, about 5.0 mm long and 3.0 mm diameter at widest; rounded apex and truncate base; color nearest RHS 154C.

Androecium:

*Filaments*.—Six, approximately 4.0 cm long and 1.0 mm in diameter; curved upward in the apical 5.0 mm; color nearest RHS 11A with basal 1.5 cm nearest RHS 155C.

*Anthers*.—Elliptic; dorsifixed, longitudinally dehiscent; about 3.5 mm long and 1.0 mm wide; color nearest RHS N187C toward middle and nearest RHS 187B along margin.

*Pollen*.—Abundant; elliptic, less than 0.1 mm long; color nearest RHS 13A.

Peduncle: Terete; usually one per mature division and thirteen per plant; glaucous, glabrous; slightly drooping to outwardly; about 38.0 cm tall, and up to 8.0 mm in diameter at base; average about 30.0 cm and 7.0 mm diameter, flowering portion about 6.0 to 8.0 cm long;

Peduncle color: When flowering nearest RHS 138C without glaucous bloom and a blend between RHS 122B and RHS 139B with glaucous bloom;

Pedicel: Glabrous; glaucous; terete; secured; approximately 17.0 mm long and 2.0 mm diameter; attitude outwardly; decreasing in size distally;

Pedicel color: Distal portion between RHS 85C and RHS 84D, base between RHS 147D and RHS 147C;

Fruit: Rare; oblong ellipsoid, tri-valved dehiscent capsule; about 1.8 cm long and 5.0 mm diameter; color when mature nearest RHS 161C;

Seed: Typically about 37 seeds per capsule 6 viable; endospermic; flattened-elliptic wing surrounding embryo situated toward one end of ellipse; about 7.0 mm long and 2.0 mm wide and 1.0 mm thick at embryo; embryo portion about 3.0 mm long, 2.0 mm wide and 1.0 thick; color nearest RHS 202A;

Disease tolerance and resistance: The new plant has not shown any resistance to pests and diseases common to *hostas*. The plant grows best and shows best coloration with plenty of moisture, adequate drainage and light shade, but is able to tolerate some drought when mature, and tolerates direct sun without leaf burn, especially during the cooler parts of the day and when provided sufficient water. Hardiness at least from USDA zone 3 through 9, and other disease resistance is typical of that of other *hostas*.

It is claimed:

1. A new and distinct ornamental plant cultivar named *Hosta* 'Waterslide' as herein described and illustrated.

* * * * *